United States Patent [19]

Hernandez

[11] Patent Number: 4,938,354
[45] Date of Patent: Jul. 3, 1990

[54] DEVICE FOR HOLDING A MEDICAL SYRINGE

[76] Inventor: Manuel F. Hernandez, 3515 Kemp, El Paso, Tex. 79904

[21] Appl. No.: 404,556

[22] Filed: Sep. 8, 1989

[51] Int. Cl.$^5$ .................... A61M 5/325; B65D 83/00
[52] U.S. Cl. .................................. 206/365; 604/192; 604/263
[58] Field of Search ................ 604/192, 263; 206/365

[56] References Cited

U.S. PATENT DOCUMENTS

| | | | |
|---|---|---|---|
| 3,226,007 | 12/1965 | Thies et al. | 206/365 X |
| 4,332,323 | 6/1982 | Reenstierna | 206/365 |
| 4,559,042 | 12/1985 | Votel | 604/263 X |
| 4,742,910 | 5/1988 | Staebler | 604/192 X |
| 4,844,249 | 7/1989 | Coulombe | 206/365 X |
| 4,846,803 | 7/1989 | Emerson | 206/365 |

FOREIGN PATENT DOCUMENTS 2198644 6/1988 United Kingdom ................ 604/192

*Primary Examiner*—William Price
*Attorney, Agent, or Firm*—Gipple & Hale

[57] ABSTRACT

A medical syringe holder is described which comprises a base for holding a hollow syringe needle holder in an inclined position and having an annular elastic collar for engaging and retaining the needle cover when the syringe is withdrawn from the device.

2 Claims, 3 Drawing Sheets

DEVICE FOR HOLDING A MEDICAL SYRINGE

SUMMARY OF THE INVENTION

The present invention is directed to a holder for a medical syringe needle. More particularly, the present invention is directed to a device for facilitating the transportation and use of one or more syringes which contain medication to be administered by injection to individuals. The device of the invention also permits the rapid labeling and identification of medication in dosages in the syringes and allows the health care personnel to administer the medication and safely dispose of the used syringe using only a single hand for the entire operation thereby minimizing the likelihood of accidental needle punctures and freeing up the health care worker's other hand for other operations.

BACKGROUND OF THE INVENTION

Increasing concern with regard to the administering of proper medications and dosages in medical treatment facilities as well as an increasing awareness of the hazards from communicable diseases which can be transmitted from accidental syringe needle punctures has made it increasingly important to provide a technology for efficiently and safely holding and transporting syringes which have been charged with the appropriate medication. It is equally important that the charged syringes be readily and easily available to the health care worker who is administering the injection so that they can be removed rapidly with a single hand and subsequently disposed of safely after the medication has been administered.

While various devices have been proposed in the prior art for holding syringes, these devices have for the most part had as their objective only the sheathing of the needle on the syringe and have not been designed to provide a system for safe and easy transport of the syringe which has previously been charged with the appropriate dosage of medication.

DISCUSSION OF THE PRIOR ART

U.S. Pat. No. 4,742,910 to Staebler describes a needle sheath holder which is adapted to be held in the hand of a medical technologist during sheathing and unsheathing of needles.

U.S. Pat. No. 4,332,323 to Reenstierna describes a device for the destruction of a hypodermic syringe needle which permits the needle attached a hypodermic syringe to be bent or broken so that it is no longer usable.

U.S. Pat. No. 4,559,042 to Votel describes an elongated tubular enclosure or receptacle for use with disposable syringe needles.

U.S. Pat. No. 3,226,007 to Thies et al. describes a disposable carton which is used for temporary storing and disposal of medical devices including syringes.

DETAILED DESCRIPTION OF THE INVENTION

According to the present invention, a device is described for holding and transporting a medical hypodermic syringe which comprises a base for receiving and holding a syringe needle and a holder which is essentially a hollow enclosed receptacle. Disposed within the syringe needle holder is an elongated hollow tube with an annular elastic collar at one end to engage the cover sleeve which surrounds and protects medical syringe needles. The syringe needle holder and the elongated receptacle tube rests at an inclined position in a base so that the upper end of the receptacle and the tube to which the annular elastic collar is attached project upward to receive the jacketed syringe needle. When the syringe needle is withdrawn from the elongated hollow tube, the elastic collar retains the jacket so that the needle is ready for use and does not require further manipulation. To facilitate use of the device of the invention in low light environments, the elastic collar which engages the jacket surrounding the syringe needle is conveniently provided with a reflective or phosphorescent material so that it is visible. Although the device of the present invention has been described as a unitary system, it can be formed in a series of interlocking or otherwise attached units to provide a series of syringe needle holders which can conveniently be transported from one location to another with syringes already charged with predetermined dosage of medication. Once the syringe has been used and the medication expended, the entire syringe and needle can be quickly and easily reinserted into the unit for disposal later on.

Figure 1:
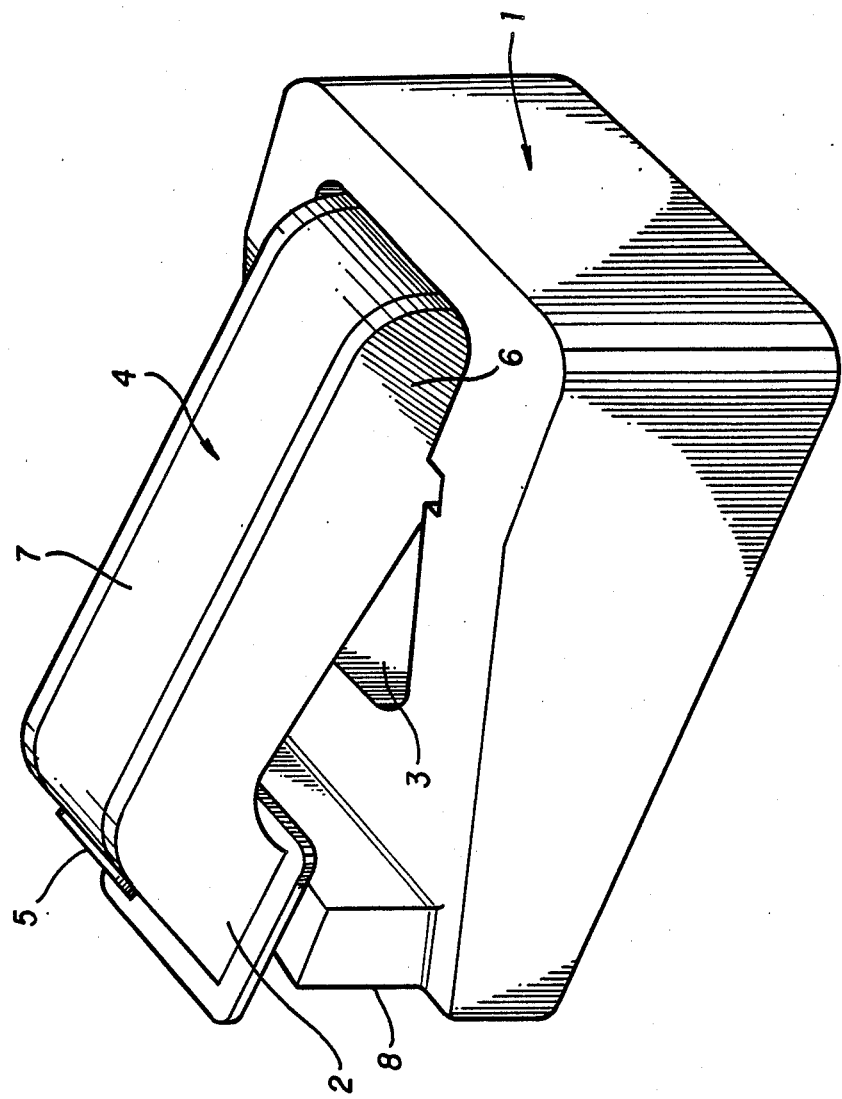
FIG. 1 is a perspective view of the device of the present invention.

The present invention will however be more completely understood by having specific reference to the drawings which illustrate a preferred embodiment thereof. Directing attention to FIG. 1 which shows a perspective view of the device of the present invention, the unit consists of a generally rectangular base 1 having a concave section 3 which accommodates the hollow enclosed syringe needle holder 2 such that the lower end of the syringe needle holder 6 is actually disposed within the recess 3. The base 1 is further provided with an upwardly extending projection or foot 8 upon which the underside of the syringe needle holder rests to provide an inclined orientation. The upper end 7 of the syringe needle holder is provided with an annular elastic collar 5 which in fact is at the mouth or opening of the elongated hollow tube disposed within the needle holding receptacle.

Figure 3:
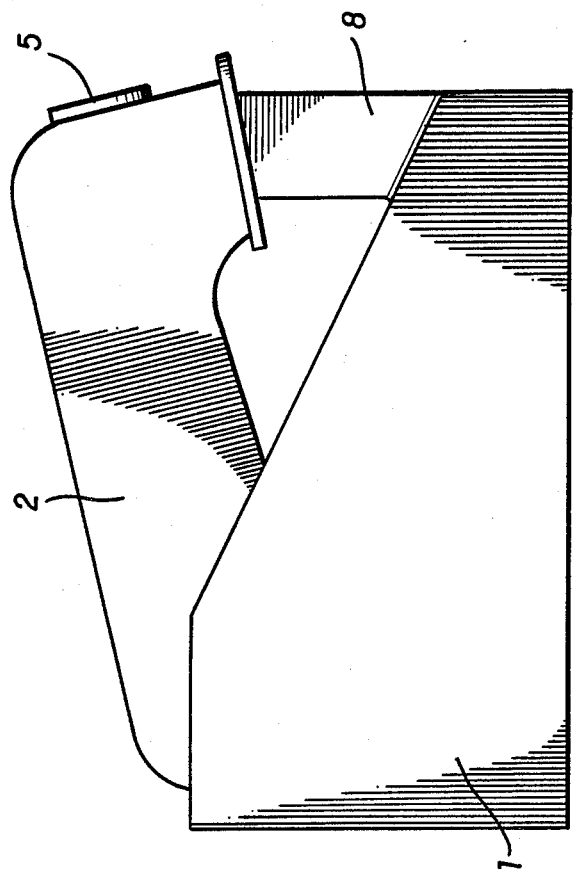
FIG. 3 is a side plan view of the device of the present invention.
Figure 2:
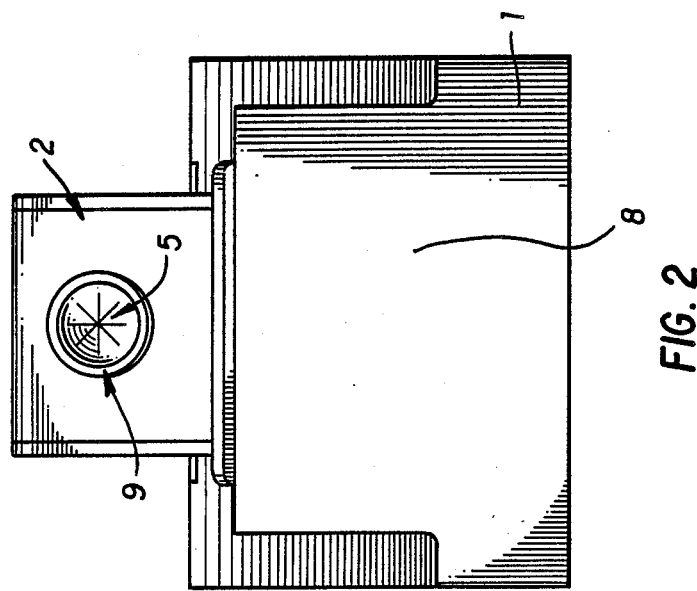
FIG. 2 is a front plan view of the device of the present invention.

Directing attention to FIGS. 2 and 3 of the drawings, the elastic collar 5 is illustrated showing the centrally disposed aperture for receiving and retaining the jacket surrounding the syringe needle. An additional annular ring 9 is provided of luminescent material to assist in identifying the aperture and surrounding collar in low light situations. This ring can for example be made of a luminescent or phosphorescent material or a highly reflective material which facilitates illumination when lighting is poor such as in rooms employed to read x-rays.

Figure 4:
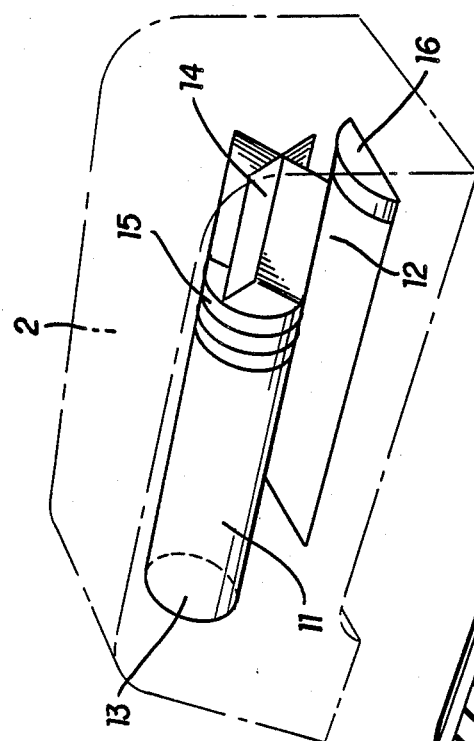
FIG. 4 is a cutaway section illustrating the hollow enclosed receptacle of the invention with the cylindrical needle holding unit disposed therein.
Figure 5:
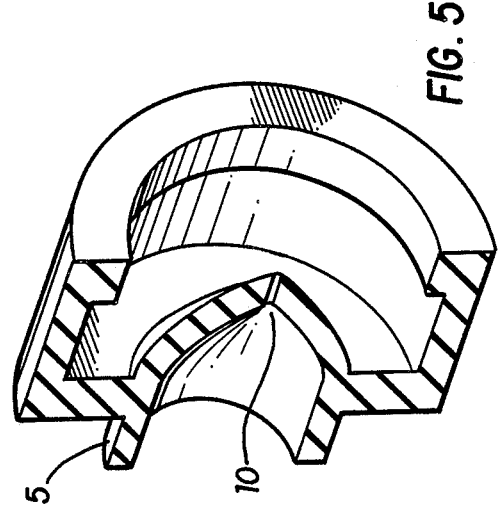
FIG. 5 is a cutaway side view of the annular elastic collar which fits in the end of the elongated syringe needle holder and which retains the needle cover when the syringe needle is withdrawn from the unit.

Directing attention to FIG. 4 of the drawings, the syringe needle holder 2 is depicted in a cutaway drawing as showing the hollow elongated tube 11 disposed therein. Conveniently, a base member 16 is provided at the bottom of the needle holder for supporting the hollow tube 11. The remote end of the tube 11 is fitted with a structure 14 that attaches to the support 16. Although not shown in FIG. 4 of the drawings, the end 13 of the hollow tube 11 is adapted to receive the elastic collar which engages and retains the jacket which is conventionally used to protect and envelope the needle of syringes. As shown in FIG. 5 of the drawings, this annular collar which fits within the tube 11 is provided with a constricted neck 10 which forms a small orifice into which the syringe needle and its surrounding jacket can be inserted. Upon withdrawal of the syringe needle, the jacket is however retained by the constricted neck 10 so that the needle jacket actually remains within the orifice. Once the syringe has been used, the needle can be returned conveniently to the jacket retained in the orifice 10 with only the need for the use of one hand.

Although not illustrated in the drawings, it is convenient to provide the base 1 of the device of the invention with a friction material such as felt which facilitates engagement on the surface on which the device is placed and avoids movement of the device when the needle is being withdrawn or replaced. It will further be appreciated that the device of the present invention can easily be fabricated of a number of materials such as plastic or metal. Preferably however, the unit is made of lightweight plastic with a felt or rubber bottom to prevent slipping. The weight of a typical single unit is therefore about four ounces so that the device can easily be carried about with the precharged syringes ready for use. The invention therefore has considerable utility both in the transport of syringes which have been prepared for use with medication and to prevent needle sticks which can transmit contagious diseases. With the syringe needle and needle cover attached, personnel remove only the cover by inserting the needle and the cover into the holder and pulling the syringe and needle cut, leaving only the needle cover inside the holder thereby making it almost impossible for personnel to come in contact with the bare needle.

What is claimed:

1. A device for holding a medical syringe which comprises: a base adapted to receive and hold a syringe needle holder means comprising a hollow, enclosed receptacle, which is disposed in an inclined position relative to said base with its lower end resting therein; an elongated hollow tube being disposed within said receptacle with an illuminated annular elastic collar means at one end proximate the upper end of said inclined receptacle for engaging the cover surrounding a medical syringe needle when said needle and cover are inserted into said elongated tube and for retaining said cover when the syringe needle is withdrawn therefrom.

2. The device of claim 1 wherein said collar means frictionally engages and retains said needle cover.